(12) United States Patent
Choski et al.

(10) Patent No.: US 6,958,050 B1
(45) Date of Patent: Oct. 25, 2005

(54) NASAL/ORAL ASPIRATION DEVICE

(75) Inventors: Pradip V. Choski, Chatsworth, CA (US); Thomas R. Thornbury, Chatsworth, CA (US); Craig McCrary, Chatsworth, CA (US)

(73) Assignee: Neotech Products, Inc., Valencia, CA (US)

( * ) Notice: Subject to any disclaimer, the term of this patent is extended or adjusted under 35 U.S.C. 154(b) by 61 days.

(21) Appl. No.: 10/173,257

(22) Filed: Jun. 18, 2002

(51) Int. Cl.$^7$ ............................................... A61M 1/00
(52) U.S. Cl. ..................... 604/35; 604/118; 604/902
(58) Field of Search ......................... 604/35, 118, 129, 604/246, 537, 902, 266, 264; 606/107; 406/152

(56) References Cited

U.S. PATENT DOCUMENTS

| | | | |
|---|---|---|---|
| 2,185,725 A | | 1/1940 | Elliot |
| 3,319,628 A | * | 5/1967 | Halligan ..................... 604/119 |
| 3,321,087 A | | 5/1967 | Fuge et al. |
| 3,610,242 A | | 10/1971 | Sheridam et |
| 3,848,604 A | | 11/1974 | Sackner |
| 3,945,385 A | * | 3/1976 | Sackner ...................... 604/119 |
| 4,022,218 A | | 5/1977 | Riddick |
| 4,204,328 A | * | 5/1980 | Kutner ......................... 433/29 |
| 4,221,220 A | | 9/1980 | Hansen |
| 4,275,724 A | | 6/1981 | Behrstock |
| 4,334,538 A | * | 6/1982 | Juhn ............................. 604/35 |
| 4,351,328 A | | 9/1982 | Bodai |
| 4,490,138 A | | 12/1984 | Lipsky et al. |
| 4,699,138 A | * | 10/1987 | Behrstock .............. 128/207.16 |
| 4,729,765 A | * | 3/1988 | Eckels et al. ................ 604/540 |
| 4,813,926 A | * | 3/1989 | Kerwin ........................ 604/118 |
| 5,004,455 A | | 4/1991 | Greenwood et al. |
| 5,114,415 A | * | 5/1992 | Shedlock ..................... 604/319 |
| 5,496,268 A | * | 3/1996 | Perla ............................ 604/27 |
| 5,628,735 A | | 5/1997 | Skow |
| 5,848,996 A | | 12/1998 | Eldor |
| 5,876,384 A | * | 3/1999 | Dragan et al. .............. 604/264 |
| 5,921,970 A | * | 7/1999 | Vandenberg ................ 604/264 |
| 6,063,063 A | | 5/2000 | Harboe et al. |

* cited by examiner

*Primary Examiner*—Nicholas D. Lucchesi
*Assistant Examiner*—Catherine S. Williams
(74) *Attorney, Agent, or Firm*—William W. Haefliger

(57) ABSTRACT

A multi-purpose medical suctioning device, comprising a first tubular body portion, a second tubular portion operatively connected to said first tubular body portion, said second tubular portion having a flexible tip portion which has an entrance of reduced area, there being a side inlet associated with at least one of said first and second portion, to be manually blocked and unblocked to control suctioning of fluid from said tip portion entrance and through said second and first tubular portion.

10 Claims, 2 Drawing Sheets

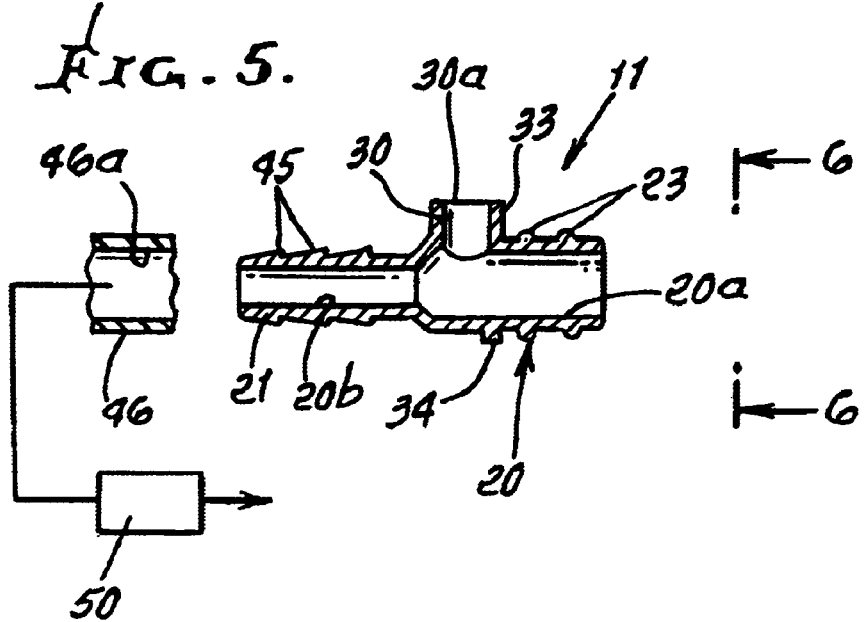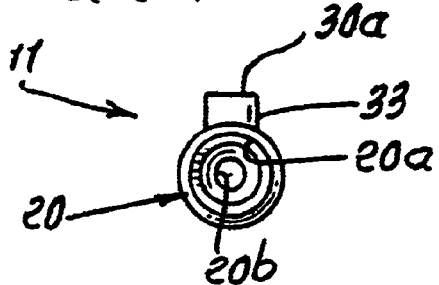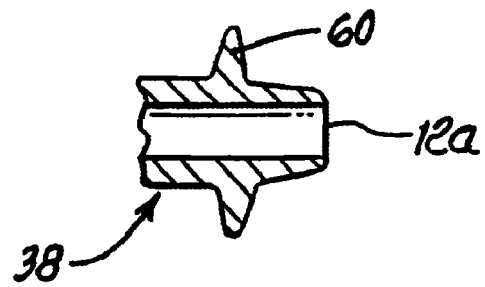

NASAL/ORAL ASPIRATION DEVICE

This application claims priority from provisional application Ser. No. 60/294,982, filed Jun. 4, 2001.

BACKGROUND OF THE INVENTION

This invention relates generally to medical suctioning or aspiration devices and methods, and more particularly to an improved device and method characterized by increased overall utility, as well as ease and effectiveness of use and operation.

There is need for improvements in devices of the type referred to above. Also, there is need for devices and methods embodying the novel and unusual features of construction, modes of operation and results found in the device and methods of use embodying in the present invention.

SUMMARY OF THE INVENTION

It is a major object of the invention to provide an improved suctioning device and method of its use, as referred to. Basically, the device comprises:

a) a first tubular body portion,
b) a second tubular portion operatively connected to said first tubular body portion,
c) the second tubular portion being easily maneuverable and having a flexible tip portion which is relatively soft and pliable,
d) there being a side inlet associated with at least one of said first and second portions, to be manually blocked and unblocked to control suctioning of fluid from the tip portion entrance and through the second and first tubular portions.

A further object is to provide such a device wherein the first tubular body portion consists of relatively hard plastic material, and said second tubular portion consists of relatively soft plastic material, the tip having an entrance of reduced suctioning area.

Yet another object is to provide the second tubular body portion with elongated flexible extent tapering toward its tip or entrance end.

Another object is to provide the second tubular portion with primary secondary and tertiary lengthwise extending sections, the primary section fitting telescopically to said first tubular body portion, said tertiary section being flexible and tapering toward its tip at a relatively lesser taper angle, and said secondary section extending between said primary and tertiary sections and at a relatively greater taper angle.

An additional object is to provide such secondary and tertiary sections to have respective lengths $L_2$ and $L_3$ wherein $L_3$ is elongated and $L_3 \gg L_2$, flexibility of said tertiary section thereby being enabled along its major elongated length, to facilitate suctioning usage of the tertiary section while the tertiary section is easily and variably bent in response to engagement with tissue of a patient, as for example nasal tissue.

A yet further object is to provide for use of such a multi-purpose medical suctioning device, by the method that includes i) providing the secondary and tertiary sections to have respective lengths $L_2$ and $L_3$ characterized in that $L_3$ is elongated relative to $L_2$, and $L_3 \gg L_2$, and
ii) providing the tertiary section to have substantially reduced overall diameter along its length relative to the overall diameter of the primary section,
iii) and providing the tertiary section to have resiliently yieldable sideward bending flexibility along its length $L_3$,
iv) and operating said device to suction fluid from a patient via said entrance tip at said tertiary section, while relatively easily sidewardly bending said tertiary section in different directions in response to sideward engagement with different parts of a patient's tissue.

These and other objects and advantages of the invention, as well as the details of an illustrative embodiment, will be more fully understood from the following specification an drawings, in which:

DRAWING DESCRIPTION

FIG. 5 is a section taken in elevation through a tubular body portion of the FIG. 1 device;

FIG. 6 is an end view taken on lines 6—6 of FIG. 5, and

FIG. 7 is a section showing a modification.

DETAILED DESCRIPTION

Figure 1:
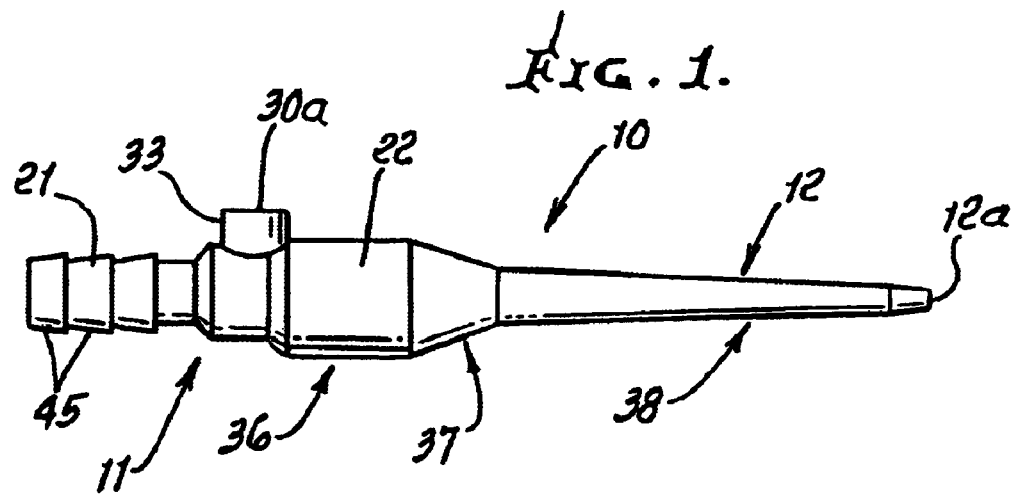
FIG. 1 is a side elevation view of a preferred device incorporating the invention.
Figure 2:
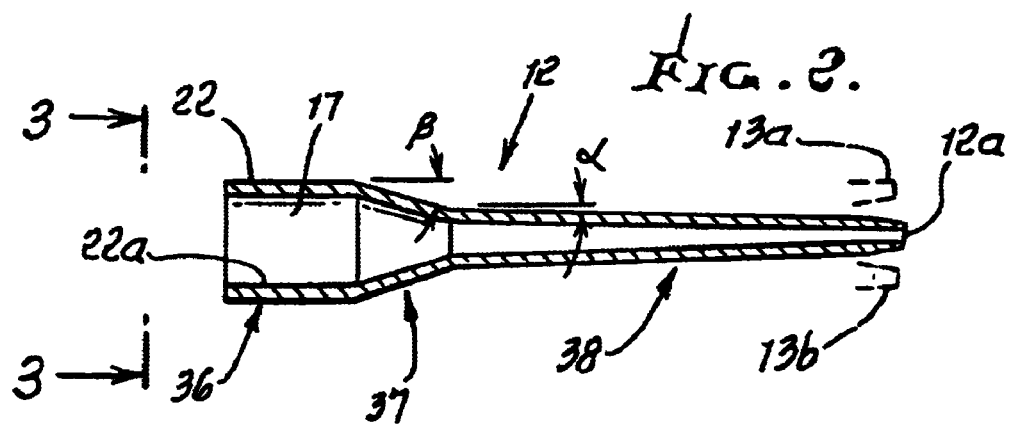
FIG. 2 is a section taken in elevation through a flexible tubular portion of the FIG. 1 device.
Figure 3:
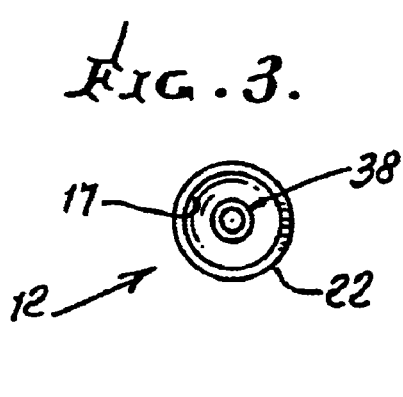
FIG. 3 is an end view taken on lines 3—3 of FIG. 2.
Figure 4:
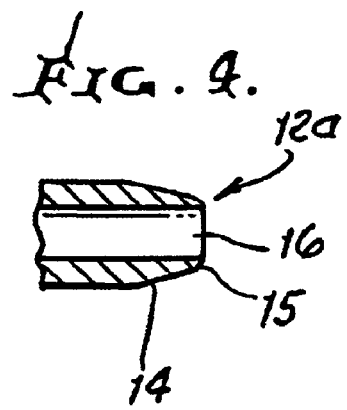
FIG. 4 is an enlarged section taken through a tip of the FIG. 2 flexible tubular portion.

In the drawings, the overall multi-purpose medical suctioning device is shown at 10, in FIG. 1. That two-part device includes a first tubular body portion 11, and a second tubular portion 12 operatively connected to, and in end alignment with the first tubular body portion. The second portion is in part sidewardly flexible, that is yieldably resistant to sideward bending, as for example would carry its tip 12a to various sidewardly deflected positions as indicated at 13a, 13b. Tapered tubular tip 12a, as seen in FIG. 4, is soft and pliable, so that it flexes easily and helps provide better access to nasal and oral cavities, with less trauma to body tissues at said orifices. Note smoothly curved or tapered annular surfaces at 14 and 15. The tubular fluid entrance is indicated at 16, which is substantially reduced in area relative to the cross sectional area at 17 of the portion 12.

The first tubular body portion 11, to which portion 12 is telescopically connected, consists of relatively hard non-deformable plastic material, whereas portion 12 flexibly and resiliently yieldably deformable, sidewardly, as referred to. Portion 11 which may be manually gripped in use, has a primary section 20 with relatively large bore 20a, and a secondary section 21, with a relatively reduced bore 20b. Section 20 is adapted to fit into primary section 22 of the second tubular portion 12, with outward projections 23 on 20 typically frictionally engaging the inner bore wall 22a of 22, for axial retention, whereby bodies 11 and 12 retained in coaxial interfitting relation.

A side inlet 30 is provided on section 20, as may be defined by a short tubular projection 33 from one side of 20, and facilitating finger control of suctioning, as by closing or opening the inlet at its outer end 30a. Another projection on section 20 is provided at 34, at the opposite side of 20 from projection 33, and these two projections provide stops, limiting telescopic endwise of 11 and 12.

It will further be noted that the second tubular body portion 12 has primary, secondary and tertiary sections 36, 37 and 38, in lengthwise axial sequence. Section 36 is sized to closely fit over section 20 as referred to, retaining section 36 against sideward bending, whereas tertiary section 38 has bending flexibility as referred to and tapers toward tip 12a at a relatively small or lesser tape angle α. Secondary section 37 extends between 36 and 38 at a relatively larger taper angle β.

Sections 37 and 38 have respective lengths $L_2$ and $L_3$, wherein $L_3$ is elongated and $L_3>>>L_2$.

Sideward bending flexibility of section 38 is thereby endless along its major elongated length $L_3$, to facilitate suctioning usage as during tip flexing in response to sideward engagement with patient tissue, as at a nostril wall, or other body orifice wall. Thus, the device is enabled to be easily and comfortably operated to suction fluid from a patient via tip 12a and the tertiary section 38 while relatively easily sidewardly bending said tertiary section in different directions in response to sideward engagement with different parts of a patient's tissue.

FIG. 5 also shows barbs 45 projecting outwardly from wall section 21 of body 11, to frictionally engage the bore 46a of a plastic tube 46, fitted endwise over 21. A source of suction (reduced pressure as provided by a pump for example) is indicated at 50.

FIG. 7 shows a modification of 12, wherein a soft pliable flange 60 is molded onto the section 38, near tip 12a, for sideward positioning engagement with a nostril inner wall, and seal off (or partially seal off) the nostril, increasing suction in the nostril.

Additional features and advantages of the invention include the following:

a) the relatively short length $l_3$ of the soft-tip or section 38 allows easy maneuvering in confined space, such as a neonatal incubator. Length $l_3$ is preferably between 1.5 and 3.5 inches.

b) One handed use procedure is enabled; i.e. with such a suction catheter control of the suction is by or with one hand, and the tip of the device is controlled with the other hand, i.e., tip location and bending.

c) The device is preferably translucent or transparent for easy visualization as during use. Prior devices are not transparent.

d) Preferably, only one orifice is provided at the tip, as at 16. This unique feature allows sealing of the device against the nostril, for proper suctioning. Prior devices lack this feature.

e) The material of the device is neither too flexible (like vinyl tubing) nor too rigid (like polypropylene) whereby the device and especially section 38 is easily maneuverable.

f) The inside cross-section is typically smallest at the tip. Therefore, material that is sucked into the device encounters less resistance to flow once it enters the tip, due to highest flow velocity at lesser cross sectional area. Thus there will be no hang ups of, or blockages by, secretions, within the product.

g) The device consists of molded plastic material that excludes vinyl and latex.

h) Endwise assembly of the two parts 11 and 12 is mechanical, for or by frictional retention. Therefore, no adhesive or glue is required, and cost is reduced or minimized.

i) Tip 12a is rounded or convex, so that engagement with sensitive tissue as in a nostril is less traumatic to patients. There are no sharp edges at the tip.

j) Both oral and nasal suction can be achieved using this one device, due to its tip configuration.

k) There is no vagal response from a patient, because of the short length of the section 38. For example, the hand-held device cannot penetrate too deeply (and uncomfortably) into the throat.

l) As compared to use of a bulb-syringe, the device does not harbor fluids or germs.

m) The devices can be easily cleaned, between uses, if re-use is necessary.

What is claimed is:

1. A multi-purpose medical suctioning device, comprising a) a one piece first tubular body portion, b) a one piece second tubular portion operatively connected to said first tubular body portion, c) said second tubular portion having a flexible tip portion which is relatively soft and pliable and has an entrance of reduced area, said second tubular portion being easily maneuverable as by bending, d) there being a side inlet associated with at least one of said first and second portions, to be manually blocked and unblocked to control suctioning of fluid from said tip portion entrance and through said second and first tubular portions, e) and wherein said first tubular body portion consists of relatively hard plastic material, and said second tubular portion consists of relatively soft plastic material, the tip being maneuverable as by one hand of the user, while the user's other hand controls said side inlet, f) said second tubular portion having primary secondary and tertiary lengthwise extending sections, said primary section fitting telescopically to said first tubular body portion, and with friction, said tertiary section being flexible and tapering toward said tip at a relatively lesser taper angle, and said secondary section extending between said primary and tertiary sections, at a relatively greater taper angle, said primary section fitting over said first tubular body portion to define a device maximum diameter proximate the entrance of said side inlet and between said inlet and said flexible tip portion, for finger control of the device including finger control of said inlet and control of said primary section to control tip portion bending, g) said secondary and tertiary sections having respective lengths $L_2$, and $L_3$ where $L_3$ is elongated and $L_3>>L_2$, flexibility of said tertiary section thereby being enabled along its major elongated length, to facilitate suctioning usage of the tertiary section as the tertiary section is easily bent in response to engagement with tissue of a patient, h) and wherein said device is characterized by one of the following:

i) said body portions are transparent ii) said body portions are translucent iii) at least one of said body portions is transparent iv) at least one of said body portions is translucent.

2. The device of claim 1 including a suctioning source operatively connected to said first tubular body portion.

3. The device of claim 1 wherein said side inlet is carried by said relatively hard plastic first tubular body portion in offset relation to a relatively enlarged end of said second tubular portion.

4. The device of claim 1 wherein said first tubular body portion extends telescopically into said relatively large end of said second tubular portion.

5. The device of claim 4 wherein said second tubular portion has elongated flexible extent tapering toward said tip.

6. The device of claim 1 wherein said primary and secondary sections are translucent.

7. The device of claim 1 including a soft pliable flange on said tertiary section near said tip.

8. The device of claim 1 wherein said tip portion entrance is the only entrance at said tip portion.

9. The device of claim 1 wherein said tip portion entrance has a cross sectional flow area which is the least cross sectional flow area of said second tubular portion.

10. The device of claim 1 wherein said body portions consist of molded plastic material that excludes vinyl and latex.

* * * * *

(12) INTER PARTES REVIEW CERTIFICATE (2196th)
United States Patent
Choksi et al.

(10) Number: US 6,958,050 K1
(45) Certificate Issued: Jul. 15, 2021

(54) NASAL/ORAL ASPIRATION DEVICE

(75) Inventors: Pradip V. Choksi; Thomas R. Thornbury; Craig McCrary

(73) Assignee: NEOTECH PRODUCTS, INC.

Trial Number:

IPR2019-00246 filed Nov. 9, 2018

Inter Partes Review Certificate for:

Patent No.: 6,958,050
Issued: Oct. 25, 2005
Appl. No.: 10/173,257
Filed: Jun. 18, 2002

The results of IPR2019-00246 are reflected in this inter partes review certificate under 35 U.S.C. 318(b).

INTER PARTES REVIEW CERTIFICATE
U.S. Patent 6,958,050 K1
Trial No. IPR2019-00246
Certificate Issued Jul. 15, 2021

AS A RESULT OF THE INTER PARTES REVIEW PROCEEDING, IT HAS BEEN DETERMINED THAT:

Claims 1-10 are cancelled.

\* \* \* \* \*